(12) United States Patent
Gulyar et al.

(10) Patent No.: US 12,290,698 B2
(45) Date of Patent: May 6, 2025

(54) THERAPEUTIC IRRADIATION DEVICE

(71) Applicant: FIELDPOINT (CYPRUS) LIMITED, Nicosia (CY)

(72) Inventors: Sergiy Alexander Gulyar, Kyiv (UA); Viktor Vasilevich Taranov, Kyiv (UA)

(73) Assignee: Fieldpoint (Cyprus) Limited (CY)

( * ) Notice: Subject to any disclaimer, the term of this patent is extended or adjusted under 35 U.S.C. 154(b) by 0 days.

(21) Appl. No.: 17/436,747

(22) PCT Filed: Oct. 30, 2019

(86) PCT No.: PCT/EP2019/079653
§ 371 (c)(1),
(2) Date: Sep. 7, 2021

(87) PCT Pub. No.: WO2021/083507
PCT Pub. Date: May 6, 2021

(65) Prior Publication Data
US 2022/0257967 A1 Aug. 18, 2022

(51) Int. Cl.
*A61N 5/06* (2006.01)
(52) U.S. Cl.
CPC ........ *A61N 5/06* (2013.01); *A61N 2005/0628* (2013.01); *A61N 2005/0659* (2013.01)
(58) Field of Classification Search
CPC .............. A61N 5/06; A61N 2005/0628; A61N 2005/0659; A61N 2/002; A61N 2/06;
(Continued)

(56) References Cited

U.S. PATENT DOCUMENTS 5,001,608 A 3/1991 Kehrli et al.
5,394,452 A * 2/1995 Swerdloff ............ A61N 5/1048
378/65
(Continued)

FOREIGN PATENT DOCUMENTS

CN 107050655 A1 8/2017
CN 109073542 A 12/2018
(Continued)

OTHER PUBLICATIONS

"Multi Luminaire, How Many Watts for Each Room in Your Home?, May 29, 2023, Multi Lighting" (Year: 2023).*
(Continued)

*Primary Examiner* — Joseph M Dietrich
*Assistant Examiner* — Michael T. Holtzclaw
(74) *Attorney, Agent, or Firm* — BARNES & THORNBURG LLP; Jeffrey R. Stone

(57) ABSTRACT

A therapeutic irradiation device may include: a source configured to emit electromagnetic radiation in a predetermined spectral range, a sensor configured to detect electromagnetic radiation in the predetermined spectral range of the electromagnetic radiation emitted by the source and to output a signal indicative of a power of the detected radiation, and a controller configured to monitor a magnitude of the signal output by the sensor and to compare the magnitude of the signal with a predetermined magnitude range, wherein the controller is configured to identify a time period during which the magnitude of the signal output by the sensor is included in the predetermined range.

20 Claims, 5 Drawing Sheets

(58) Field of Classification Search
CPC .... A61N 2005/0626; A61N 2005/0627; A61N 5/0616; A61N 2/004; A61N 2/008; A61N 2005/0642

See application file for complete search history.

(56) References Cited

U.S. PATENT DOCUMENTS

| | | | |
|---|---|---|---|
| 7,730,893 | B2 | 6/2010 | Dougal |
| H2242 | H | 7/2010 | Gonzales |
| 8,080,047 | B2 | 12/2011 | Yu |
| 2008/0004611 | A1* | 1/2008 | Houbolt ............... A61B 5/0059 606/9 |
| 2009/0110933 | A1 | 4/2009 | Hyde et al. |
| 2012/0226268 | A1* | 9/2012 | Liu ...................... A61N 5/0613 606/9 |
| 2012/0296150 | A1 | 11/2012 | Pletnev et al. |
| 2012/0330387 | A1* | 12/2012 | Ferraz Rigo ......... A61N 5/0618 250/206 |
| 2014/0003973 | A1 | 1/2014 | Arai et al. |
| 2014/0039473 | A1* | 2/2014 | Liu ...................... A61N 5/0616 606/9 |
| 2016/0129279 | A1 | 5/2016 | Ferolito |
| 2016/0158568 | A1 | 6/2016 | Uplaznik et al. |
| 2016/0287897 | A1 | 10/2016 | Kaestle |
| 2017/0172660 | A1* | 6/2017 | Mehl .................... A61B 18/203 |
| 2018/0015298 | A1 | 1/2018 | Iguchi et al. |
| 2018/0116421 | A1 | 5/2018 | Goncalves |
| 2019/0090767 | A1* | 3/2019 | Sako ........................ G01J 3/42 |
| 2019/0351252 | A1* | 11/2019 | Taboada ............... A61N 5/0618 |
| 2020/0179714 | A1* | 6/2020 | Zanata ................. A61N 5/0613 |
| 2022/0387819 | A1 | 12/2022 | Lim |

FOREIGN PATENT DOCUMENTS

| | | |
|---|---|---|
| EP | 0311125 A1 | 4/1989 |
| EP | 3037131 A2 | 6/2016 |
| JP | 2005296504 A2 | 10/2005 |
| WO | 2005/000389 A2 | 1/2005 |
| WO | 2006/131997 A1 | 12/2006 |
| WO | 2012/085805 A2 | 6/2012 |
| WO | 2015/075610 | 5/2015 |
| WO | 2016/007798 | 1/2016 |
| WO | WO-2016064293 A1 * | 4/2016 ............... A61N 5/06 |
| WO | 2016/127120 A1 | 8/2016 |

OTHER PUBLICATIONS

International Search Report issued in related PCT application No. PCT/EP2019/079653, dated Jan. 7, 2020.
UCMS, Journal of US-China Medical Science, vol. 14, No. 2, Mar.-Apr. 2017 (Serial No. 106).
UCMS, Journal of US-China Medical Science, vol. 14, No. 4, Jul.-Aug. 2017 (Serial No. 108).
Office Action Issued by The Eurasian Patent Organization (EAPO), Application No. 202193233, mailing date Oct. 6, 2022. English translation included.
Examination Report and the Written Comments of the Examining Body issued by Iranian Patent Office for Application140050140003005401 (PCT/EP2019/079653), date of application registration Oct. 2, 2021.
Notice of Reasons for Rejection issued in Japanese Patent Application No. 2021-568787, dated May 9, 2023.
English translation of Notice of Reasons for Rejection issued in Japanese Patent Application No. 2021-568787, dated May 9, 2023.
First Examination Report issued by the Indian Patent Office for application No. 202117048559, dated May 22, 2024.
Request for the Submission of an Opinion issued by the Korean Patent Office for application No. 10-2021-7035577, dated Jun. 19, 2024.
Substantive Examination Report issued by the Chinese Patent Office for application No. 521430259, dated Jul. 11, 2024.
Substantive Examination Report issued by the Saudi Arabian Patent Office, dated Nov. 16, 2023. English translation attached.
Examination report No. 1 issued by IP Australia, dated Nov. 4, 2024. For informational purposes only.
Notice of Deficiencies for Patent Application No. 292089 issued by the Israeli Patent Office, dated Aug. 13, 2024. For informational purposes only.
Preliminary Conclusion (on non-Patentability) issued by the Ukraine Patent Office for Application No. 2022 01775, dated Oct. 18, 2024. For informational purposes only.

* cited by examiner

THERAPEUTIC IRRADIATION DEVICE

TECHNICAL FIELD

Various embodiments relate generally to a therapeutic irradiation device.

BACKGROUND

Light therapy has gained significant importance in the past few years, in particular in the therapy of—but not limited to—skin diseases. In this field, it is generally recognized that the therapeutic effect is closely related to the characteristics of the light used for therapy, including for example the wavelength range of the light, and to the light dose. Therefore, the therapeutic effect of light therapy is determined by the ability of controlling both the wavelength of the light used for light therapy and the light dose.

Exemplary therapeutic irradiation devices are disclosed inter alia in EP 3 037 131 A2, WO 2016/127120 A1, WO 2005/000389 A2, US 2016/0158568 A1 WO 2012/085805 A2, EP 0 311 125 A1, and U.S. Pat. No. 5,001,608.

SUMMARY

According to the present disclosure, a therapeutic irradiation device is provided. The therapeutic irradiation device may include: a source configured to emit electromagnetic radiation in a predetermined spectral range, a sensor configured to detect electromagnetic radiation in the predetermined spectral range of the electromagnetic radiation emitted by the source and to output a signal indicative of a power of the detected radiation, and a controller configured to monitor a magnitude of the signal output by the sensor and to compare the magnitude of the signal with a predetermined magnitude range, wherein the controller may be configured to identify a time period during which the magnitude of the signal output by the sensor is included in the predetermined range.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the disclosure. In the following description, various embodiments of the disclosure will be described with reference to the following drawings, in which.

DETAILED DESCRIPTION

The following detailed description refers to the accompanying drawings that show, by way of illustration, specific details and embodiments in which the invention may be practiced.

The word "exemplary" is used herein to mean "serving as an example, instance, or illustration", Any embodiment or design described herein as "exemplary" is not necessarily to be construed as preferred or advantageous over other embodiments or designs.

Figure 1:
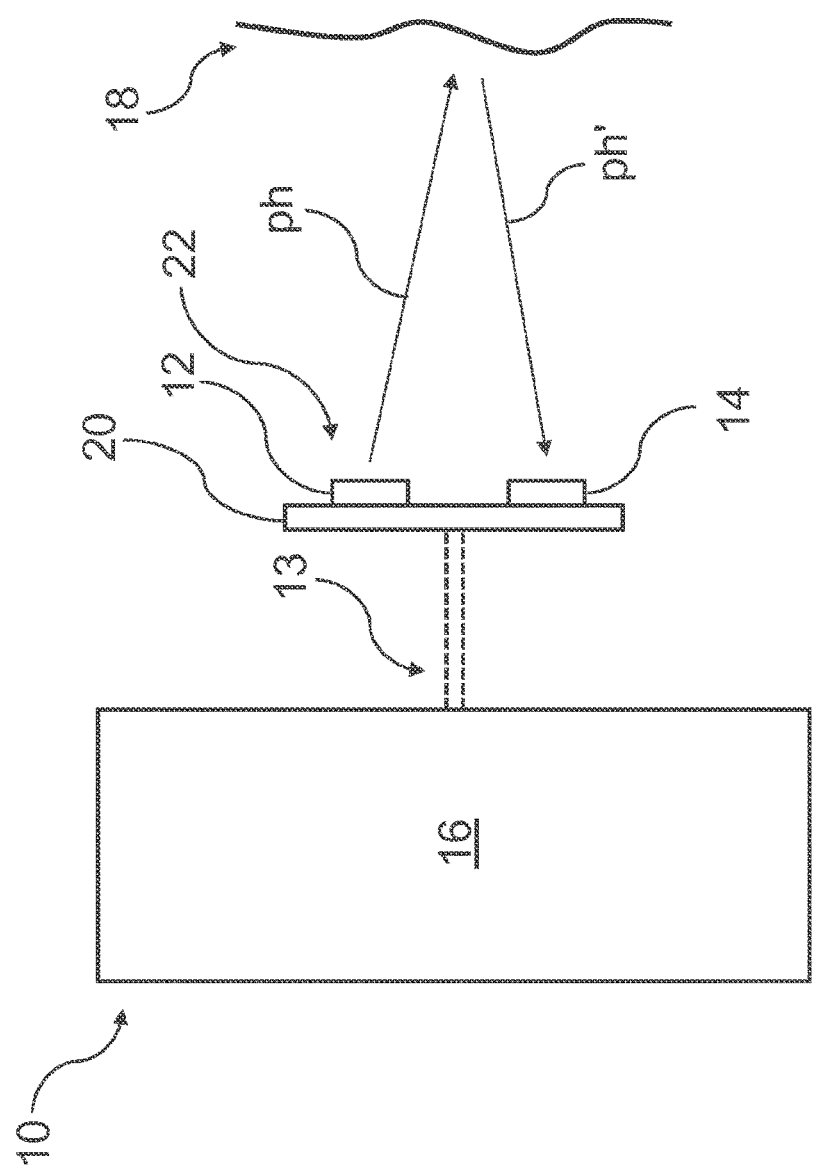
FIG. 1 is a schematic drawing illustrating a therapeutic irradiation device according to an exemplary embodiment of the present disclosure.

FIG. 1 is a schematic view illustrating a therapeutic irradiation device 10 according to an exemplary embodiment of the present disclosure. The irradiation device 10 may include a source 12, a sensor 14, and a controller 16.

The source 12 may be configured to emit electromagnetic radiation ph in a predetermined spectral range (wavelength range). The sensor 14 may be configured to detect electromagnetic radiation in the predetermined spectral range of the electromagnetic radiation ph emitted by the source 12 and to output a signal indicative of a power of the detected radiation. As indicated in FIG. 1, during a therapy session, the irradiation device 10 is positioned adjacent to a subject (e.g. a person) 18 to be treated. In this configuration, electromagnetic radiation ph emitted by the source 12 is reflected by the subject 18 and a part of the reflected radiation ph' is reflected towards the sensor 14.

The sensor 14 may be configured as an irradiance sensor and the signal output by the sensor may be indicative of irradiance. Irradiance is the radiant power received per unit area (SI unit: $W/m^2$).

The source 12 and the sensor 14 may be electrically connected to the controller 16 via signal lines 13. The controller 16 may be configured to control the operation of the source 12 and of the sensor 14. The sensor 14 may be configured to transmit the signal indicative of the power of the detected radiation ph' to the controller 16 via the signal lines 13, The signal output by the sensor 14 may be a current signal or voltage signal. The controller 16 may be configured to determine a magnitude of the signal output by the sensor 14, to monitor the magnitude of the signal output by the sensor, and to compare the magnitude of the signal with a predetermined magnitude range, wherein the controller may be configured to identify a time period during which the magnitude of the signal output by the sensor is included in the predetermined magnitude range.

Figure 2:
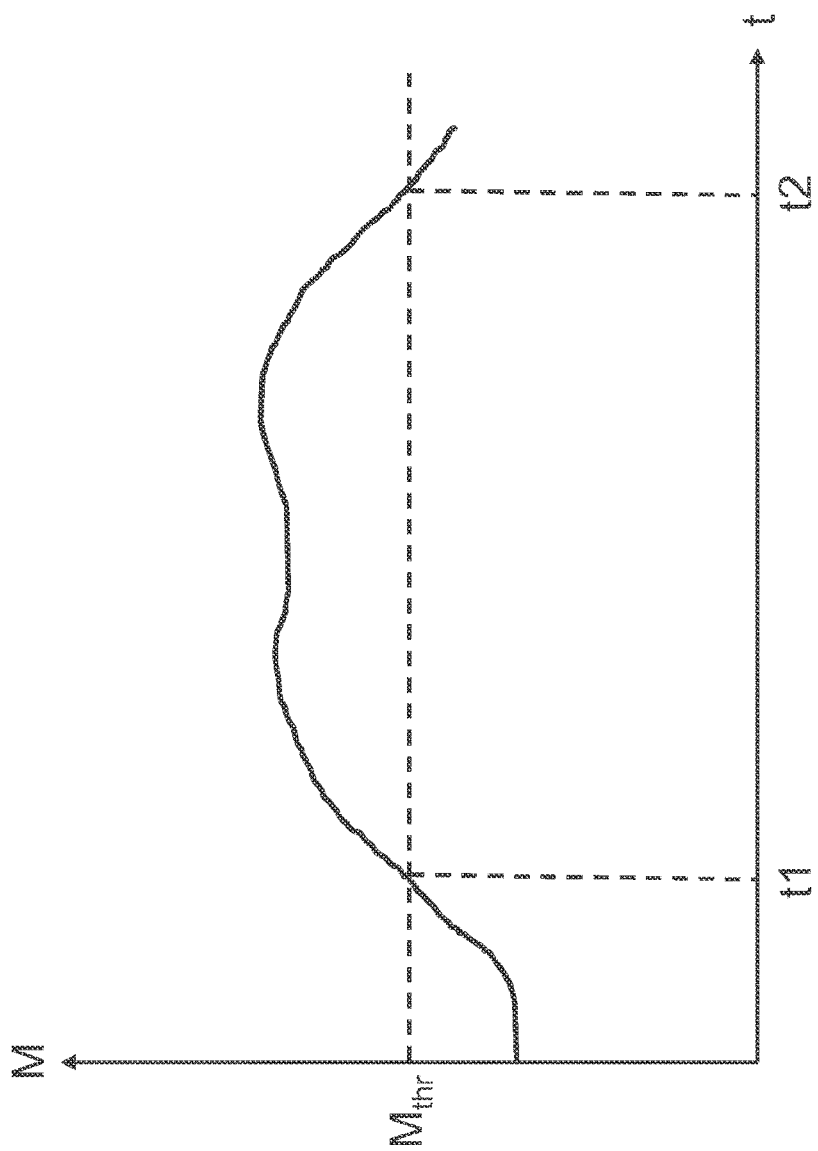
FIG. 2 is a graph schematically showing the variation of the magnitude of a signal output by a sensor of a therapeutic irradiation device according to an embodiment of the present disclosure.

The variation of the magnitude M of the signal over time t is schematically shown in FIG. 2. As indicated in FIG. 2, the controller 16 may be configured to compare the magnitude M of the signal with a threshold value $M_{thr}$, i.e. with the predetermined magnitude range above $M_{thr}$. The threshold value $M_{thr}$ may be empirically determined in advance and may be stored in a memory of the controller 16. This threshold value $M_{thr}$ may correspond to a predetermined distance between the source 12 and the subject 18 to be treated. More specifically, magnitudes lower than the threshold value $M_{thr}$ may correspond to a state in which the power of the radiation ph' received by the sensor 14 is low, which in turn means that only a small fraction of the power of the radiation emitted by the source 12 is reflected by the subject 18 towards the sensor 14. This in turn indicates that the relative position between the source 12 and the subject 18 is not suitable for the specific therapy, since the power of the radiation actually reaching the subject 18 is too low. An optimal distance between the irradiation device 10 and the subject may range between 1 and 10 cm, optionally between 1 and 5 cm.

In the exemplary graph shown in FIG. 2, the magnitude M of the signal output by the sensor 14 is higher than the threshold value $M_{thr}$ during the time period between t1 and t2, but lower than the threshold value $M_{thr}$ before t1 and after t2. Since, as set forth above, the controller 16 is configured to monitor the magnitude M of the signal and to compare the magnitude M of the signal with the threshold value $M_{thr}$, the controller 16 may be configured to identify the time period/time periods during which the magnitude M is higher than the threshold value $M_{thr}$, i.e. during which the magnitude M is included in the magnitude range above $M_{thr}$. The controller 16 may be configured to integrate the magnitude M during the period or periods of time during which the magnitude M is in the predetermined range above $M_{thr}$. This integration process yields an entity that is indicative of the amount of radiation energy deposited into the subject 18, e.g. into a portion of the skin of a person to be treated. In case the sensor 14 is configured as an irradiance sensor, this integration process yields the energy received per unit area (SI unit: $E/m^2$) and is thus indicative of the dose received by the subject 18.

In an exemplary embodiment, the controller 16 may be configured to integrate the time periods during which the magnitude M of the signal is higher than the threshold value $M_{thr}$. Under the assumption that the dose received by the subject 18 is constant in case the magnitude M is higher than $M_{thr}$, this approach may be also indicative of the dose received by the subject 18.

Consequently, by means of the irradiation device 10 according to the exemplary embodiment described above, the relative position between the source 12 and the subject 18 can be accurately monitored simply by monitoring the power of the radiation reflected by the subject 18 towards the sensor 14, i.e. towards the irradiation device 10.

As indicated in FIG. 1, the source 12 and the sensor 14 may be positioned relative to each other in a fixed positional relationship. In this way, systematic errors during the monitoring of the relative position between the irradiation device 10 and the subject 18 can be minimized, since a variation of the magnitude of the signal output by the sensor 14 can be reliably assigned to a variation of the relative position between the irradiation device 10 and the subject 18 but not to a variation of the relative position between the source 12 and the sensor 14.

As shown in FIG. 1, the source 12 and the sensor 14 may be mounted on a common carrier 20 which may be configured as a circuit board. The carrier 20, the source 12, and the sensor 14 will be collectively referred to in the following as an emission unit 22.

The controller 16 may include or may be configured as a microcontroller, an application specific integrated circuit (ASIC), or the like.

The source 12 may include at least one LED. LEDs benefit from lower power consumption as compared to halogen lamps that are employed in conventional therapeutic irradiation devices. In addition, LEDs benefit from narrow emission spectra that can only be achieved with conventional halogen lamps by using additional band-pass filters. Apart from that, conventional halogen lamps suffer from a limited durability of 600-1000 hours. Furthermore, the emission efficiency in the green and blue wavelength range of halogen lamps is limited to less than 15%.

In the previously described exemplary embodiment, the source 12 may be permanently on during the operation of the irradiation device 10 or during a therapy session to monitor the relative position between the irradiation device 10 and the subject 18. In an exemplary embodiment, the source 12 may be automatically switched off, e.g. by the controller 16, after the deposition of a predetermined dose.

Figure 3:
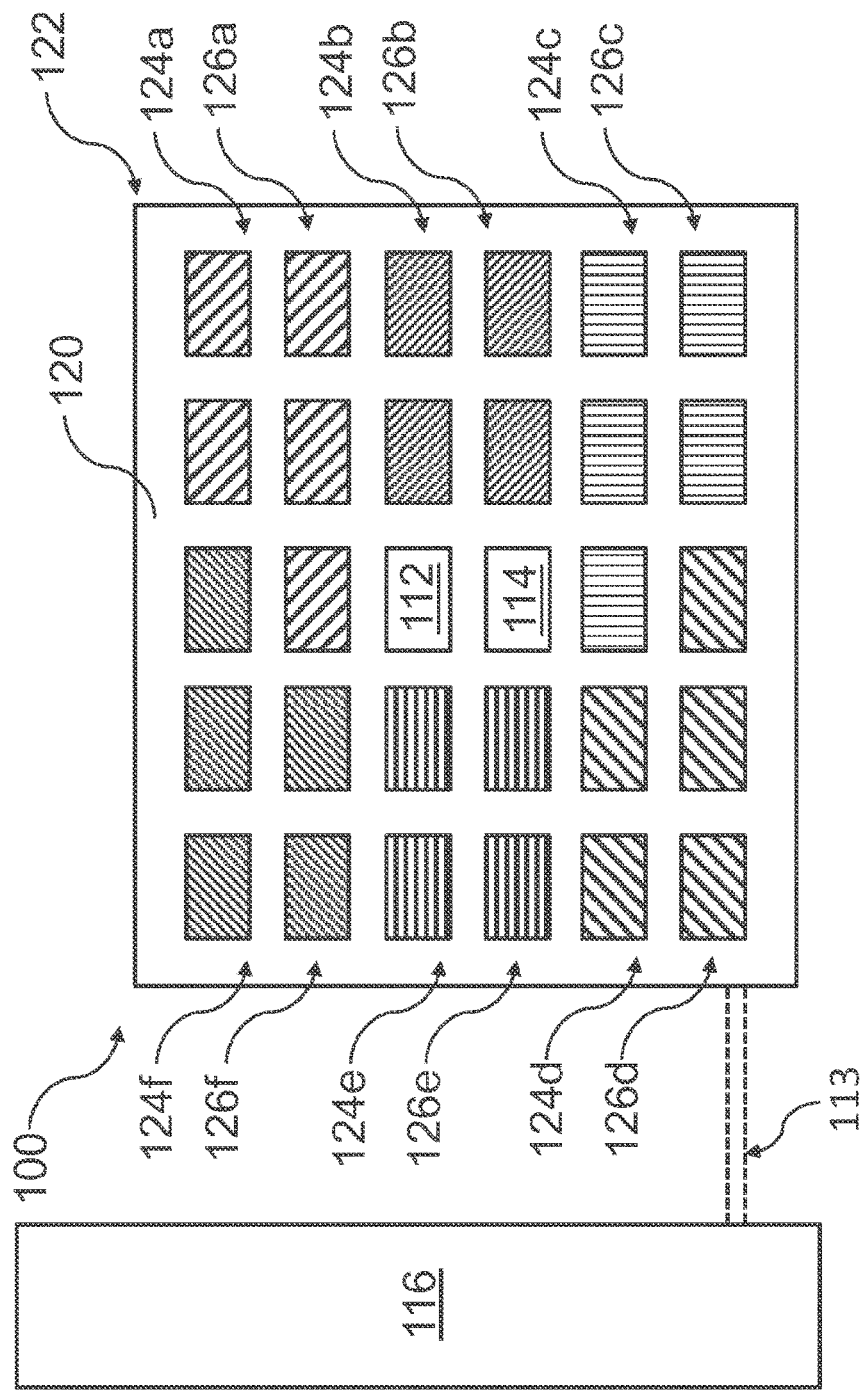
FIG. 3 is a schematic drawing illustrating a therapeutic irradiation device according to an exemplary embodiment of the present disclosure.

FIG. 3 is a schematic view of an emission unit 122 of a slightly modified exemplary irradiation device 100. The following description of the modified irradiation device 100 will focus on the differences with respect to the previously described embodiment.

Similar to the previously described embodiment, the irradiation device 100 shown in FIG. 3 includes a source 112 and a sensor 114 which may be identically configured as in the previous embodiment. In addition, the irradiation device 100 may further include at least one auxiliary source 124a, 124b, 124c, 124d, 124e, 124f configured to emit electromagnetic radiation in a wavelength range which is different from the wavelength range of the electromagnetic radiation emitted by the source 112.

As shown in FIG. 3, the irradiation device 100 may include a plurality of auxiliary sources 124a, 124b, 124c, 124d, 124e, 124f. The different hatchings in FIG. 3 indicate different types of auxiliary sources 124a, 124b, 124c, 124d, 124e, 124f that differ from each other in view of their emission spectra. The auxiliary sources 124a, 124b, 124c, 124d, 124e, 124f may be grouped into respective auxiliary source groups 126a, 126b, 126c, 126d, 126e, 126f, wherein the sources 124a, 124b, 124c, 124d, 124e, 124f of a specific auxiliary source group 126a, 126b, 126c, 126d, 126e, 126f are identical. It should be noted that the detailed arrangement of the auxiliary sources 124a, 124b, 124c, 124d, 124e, 124f and/or of the auxiliary source groups 126a, 126b, 126c, 126d, 126e, 126f in FIG. 3 is exemplary and may be arbitrarily varied, e.g. depending on specific therapeutic requirements.

Similar to the previous embodiment, the emission unit 122 may include a carrier 120 such as a circuit board, carrying the source 112, the sensor 114, and the auxiliary sources 124a, 124b, 124c, 124d, 124e, 124f in a fixed positional relationship relative to each other. The irradiation device 100 may further include a controller 116 connected to the emission unit 122 via signal lines 113.

Figure 4:
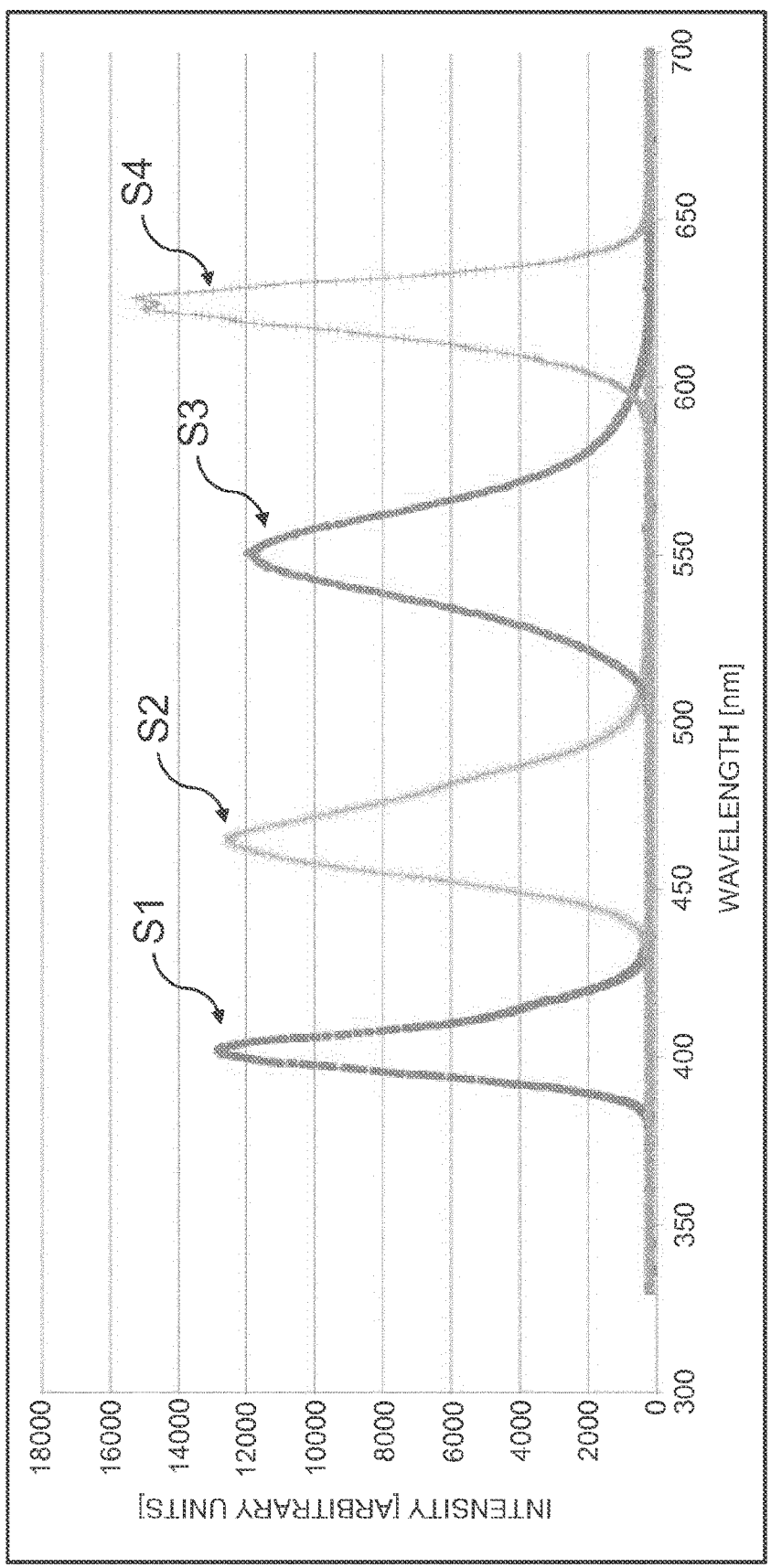
FIG. 4 is graph illustrating emission spectra of LEDs employed in a therapeutic irradiation device according to an exemplary embodiment according to the present disclosure.

The auxiliary sources 124a, 124b, 124c, 124d, 124e, 124f may also be configured as LEDs. The advantages of LEDs as compared to conventional halogen lamps have been set forth above with respect to the source 12. Exemplary emission spectra of LEDs used as auxiliary sources in a therapeutic irradiation device according to the present disclosure are shown by the graphs S1, S2, S3, S4 in FIG. 4, wherein the individual peaks correspond to different emission spectra of LEDs employed as auxiliary sources. As shown in FIG. 4, the auxiliary sources may be configured to emit visible light. Even though not shown in FIG. 4, the irradiation devices 100 may include auxiliary sources configured as LEDs that are configured to emit light in the infrared (IR) or in the ultraviolet (UV) wavelength range. LEDs configured to emit UV radiation may be used for sterilization purposes, e.g. when irradiating open wounds (for example, in the absence of an upper skin layer on the body surface in case of burns). In an exemplary embodiment, the UV LEDs may be positioned along a perimeter of the emission unit 122.

The auxiliary sources 124a, 124b, 124c, 124d, 124e, 124f may be individually controllable by the controller 116. The controller 116 may be configured to control the auxiliary sources 124a, 124b, 124c, 124d, 124e, 124f on an auxiliary source group basis. More specifically, the controller 116 may be configured to switch the auxiliary sources 124a, 124b, 124c, 124d, 124e, 124f of an individual auxiliary source group 126a, 126b, 126c, 126d, 126e, 126f collectively on or off, and independently of the auxiliary sources 124a, 124b, 124c, 124d, 124e, 124f of the other groups 126a, 126b, 126c, 126d, 126e, 126f. The controller 116 may be configured to control the auxiliary sources 124a, 124b, 124c, 124d, 124e, 124f to emit radiation in a pulsed manner at frequencies of e.g. 1 Hz to 1 kHz.

By individually controlling the auxiliary sources 124a, 124b, 124c, 124d, 124e, 124f, either on a group basis or not, the emission spectrum of the irradiation device 100 can be adapted to a specific therapeutic treatment. The irradiation device 100 may include a user interface by means of which the spectrum can be set prior to starting a therapy session.

The controller may be configured to control at least one of the auxiliary sources 124a, 124b, 124c, 124d, 124e, 124f, optionally a plurality of the auxiliary sources 124a, 124b, 124c, 124d, 124e, 124f, further optionally all of the auxiliary sources 124a, 124b, 124c, 124d, 124e, 124f, on the basis of the signal output by the sensor 114.

Similar to the irradiation device 10, the source 112 may be permanently on during the operation of the irradiation device 100, or at least during a therapy session. In this way, the position of the irradiation device 100 relative to a subject may be permanently monitored. Hence, in the embodiments of the present disclosure, the source 112 may be also referred to as a monitoring source.

The controller 116 may be configured to control the auxiliary sources 124a, 124b, 124c, 124d, 124e, 124f on the basis of the magnitude of the signal output by the sensor 114. In an exemplary embodiment, the controller 16 may be configured to control at least one of, a plurality of, or all of the auxiliary sources 124a, 124b, 124c, 124d, 124e, 124f to emit radiation only if the magnitude M of the signal output by the sensor 114 is above the threshold value $M_{thr}$, i.e. in the predetermined magnitude range above $M_{thr}$, which, as set forth above, indicates that the irradiation device 100 is positioned in close proximity to the subject.

As set forth above, the source 112 may be permanently on during the operation of the irradiation device 100 or at least during the execution of a therapy session to monitor the position of the irradiation device with respect to a subject to be treated. Hence, in an exemplary embodiment, in a case where, after switching on the source 112, the irradiation device 100 is not positioned in close proximity to a subject to be treated (i.e. the magnitude of the signal output by the sensor 114 is lower than the threshold value $M_{thr}$), none of the auxiliary sources 124a, 124b, 124c, 124d, 124e, 124f is switched on. As soon as the irradiation device 100 is positioned in close proximity to the subject to be treated such that the magnitude M of the signal output by the sensor 114 exceeds the threshold voltage $M_{thr}$, at least one of, a plurality of, or all of the auxiliary sources 124a, 124b, 124c, 124d, 124e, 124f are switched on by the controller 116. If, during a therapy session, the irradiation device 100 is moved away from the subject such that the magnitude M of the signal output by the sensor 114 drops below the threshold value $M_{thr}$, the controller 116 may switch off the auxiliary sources 124a, 124b, 124c, 124d, 124e, 124f.

If the magnitude of the signal is included in the predetermined range, i.e. if M $M_{thr}$, the controller 116 may perform an integration process to determine the dose or may at least integrate those time periods during which the magnitude M is higher than the threshold value $M_{Thr}$.

A predetermined dose or a predetermined time period for the therapy may be set prior to starting the therapy session, e.g. via a user interface. The controller 116 may be configured to stop the therapy session, i.e. to switch off the auxiliary sources 124a, 124b, 124c, 124d, 124e, 124f, and optionally also the source 112, when the predetermined dose is achieved or the predetermined time period has elapsed.

In an exemplary embodiment, the sensor 114 may be configured to detect electromagnetic radiation in the entire wavelength range of the radiation emitted by the source 112 and the auxiliary sources 124a, 124b, 124c, 124d, 124e, 124f to accurately determine the dose. In an alternative embodiment, the sensor 114 may be configured to detect electromagnetic radiation only in the wavelength range of the radiation emitted by the source 112. For this purpose, the sensor 114 may be equipped with an optical filter configured to transmit radiation only in the wavelength range of the radiation emitted by the source 112.

In an exemplary embodiment, the source 112 may be configured to emit electromagnetic radiation in a non-visible wavelength range, With this configuration and in case at least one of the auxiliary sources 124a, 124b, 124c, 124d, 124e, 124f is configured to emit light in a visible wavelength range, a person to be treated can easily recognize whether the irradiation device 100 is correctly positioned, More specifically, with such a configuration, a person to be treated will only perceive the light emitted by the at least one auxiliary source 124a, 124b, 124c, 124d, 124e, 124f configured to emit light in a visible wavelength range, but not the radiation emitted by the source 112. Further, since, as set forth above, the at least one auxiliary source 124a, 124b, 124c, 124d, 124e, 124f is turned on only if the irradiation device 100 is correctly positioned relative to the subject (person) to be treated, the person can easily recognize, if the irradiation device is correctly positioned and can, hence, keep the irradiation device 100 in the correct position. Consequently, the irradiation device 100 is configured to provide a feedback to a user regarding the correct position.

Since the source 112 may be permanently on during a therapy session, it may be advantageous to use a source 112 configured to emit radiation in a low-energetic wavelength range, preferably in the infrared wavelength range. In an exemplary embodiment the source 112 may be configured to emit infrared radiation (light) at about 900 nm.

To distinguish the radiation emitted by the source 112 from ambient radiation, the source 112 may be configured to emit electromagnetic radiation in a characteristic and unique manner, e.g. in a pulsed manner. In an exemplary embodiment, the pulse frequency may range between about 1 Hz and about 1 kHz.

In an exemplary embodiment, the source 112 may be configured to emit radiation in a very narrow wavelength range, e.g. of less than 10 nm. In addition, the source 112 may be configured to emit radiation in this narrow wavelength range with a power exceeding the power of ambient radiation in this wavelength range in a normal environment, e.g. in an environment at room temperature. This configuration is particularly preferable, in case the source 112 is configured to emit radiation in a non-visible wavelength range, e.g. in the infrared wavelength range. In such a case, the power of the infrared radiation emitted by the source in the predetermined narrow wavelength rage may be selected to be at least one order of magnitude, optionally at least two orders of magnitude, further optionally at least three orders of magnitude, higher than the power in said narrow wavelength range of the infrared radiation emitted by the surrounding, i.e. of the blackbody radiation emitted by the surrounding at room temperature.

In such a configuration, the sensor 114 may be equipped with a narrow optical bandpass filter matched to the emission spectrum of the source 112. Hence, any variation of the radiant power detected by the sensor 114 in said narrow wavelength range can be associated with a variation of the relative position between the irradiation device 100 and a subject to be treated, since variations of the power of the background radiation in said narrow wavelength range can be neglected. In this way, the relative position between the irradiation device 100 and the subject to be treated can be reliably monitored.

Figure 5:
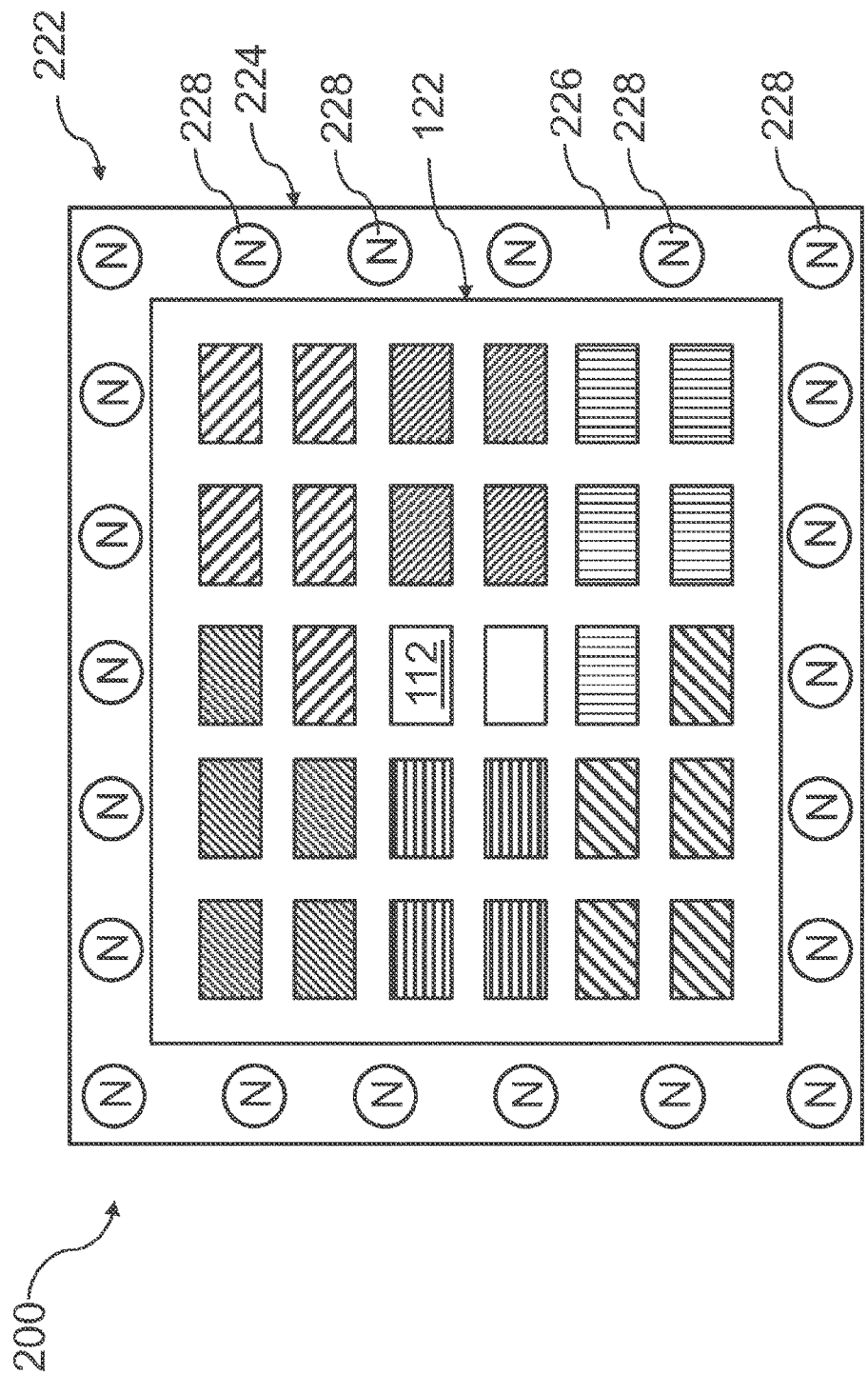
FIG. 5 is a schematic drawing illustrating an emission unit of a therapeutic irradiation device according to another exemplary embodiment of the present disclosure.

FIG. 5 is a schematic drawing illustrating an emission unit 222 of a therapeutic irradiation device 200 according to a further exemplary embodiment.

The emission unit 222 shown in FIG. 5 includes an emission unit 122 according to the previous embodiment shown in FIG. 3 and in addition a magnet assembly 224 configured to generate a magnetic field in an emission region into which electromagnetic radiation is emitted by the source 112 and/or the auxiliary sources. The emission region may be a region in front of the emission unit 222 where during a therapy session a subject to be treated should be located.

The magnetic field has an antithrombotic effect, reduces pain and inflammation, and improves the rheological properties of the blood. Hence, by means of the magnetic field generated by the magnet assembly 224, the therapeutic efficiency may be increased.

The magnet assembly 224 may include a carrier (frame) 226 made of a dielectric material and a plurality of magnets 228 supported by the carrier 226. The magnets 228 may be permanent magnets.

To generate a magnetic field in a large part of the emission region or even in the entire emission region of the source 112, the magnets 228 may be disposed to surround the source 112.

As indicated in FIG. 5, the magnets 228 may be arranged such that the north poles N of each magnet 228 faces the emission region. This configuration provides a stabilization of the domain structure of biological objects at the molecular level which leads to a stabilization of their positions and, consequently, to a high therapeutic effect.

Therapeutic irradiation devices according to the present disclosure may be employed in the field of physiotherapy by direct biostimulation of superficial cellular structures of the skin and mucous membranes, transcutaneous non-invasive action on blood formed elements, as well as distant systemic influence through biologically active areas and zones used in reflexology. Therapeutic irradiation devices according to the present disclosure may be applied in clinical practice, in cosmetology, and in rehabilitation physiotherapy for athletes.

In the following, several Examples according to the present disclosure will be described.

Example 1 is a therapeutic irradiation device including: a source configured to emit electromagnetic radiation in a predetermined spectral range, a sensor configured to detect electromagnetic radiation in the predetermined spectral range of the electromagnetic radiation emitted by the source and to output a signal indicative of a power of the detected radiation, and a controller configured to monitor a magnitude of the signal output by the sensor and to compare the magnitude of the signal with a predetermined magnitude range, wherein the controller is configured to identify a time period during which the magnitude of the signal output by the sensor is included in the predetermined range.

In Example 2, the subject matter of Example 1 can optionally further include that the controller is configured to integrate the signal output by the sensor to determine a dose, if the magnitude of the signal is included in the predetermined magnitude range.

In Example 3, the subject matter of Example 1 or 2 can optionally further include at least one auxiliary source configured to emit electromagnetic radiation in a wavelength range which is different from the wavelength range of the electromagnetic radiation emitted by the source.

In Example 4, the subject matter of Example 3 can optionally further include that the controller is configured to control the at least one auxiliary source on the basis of the signal output by the sensor.

In Example 5, the subject matter of Example 4 can optionally further include that the controller is configured to control the at least one auxiliary source such as to emit electromagnetic radiation only if the magnitude of the signal output by the sensor is included in the predetermined magnitude range.

In Example 6, the subject matter of any one of Examples 3 to 5 can optionally include a plurality of auxiliary sources.

In Example 7, the subject matter of Example 6 can optionally further include that at least two among the plurality of auxiliary sources are configured to emit electromagnetic radiation in mutually different wavelength ranges.

In Example 8, the subject matter of Example 6 or 7 can optionally include that the controller is configured to individually control the auxiliary sources of the plurality of auxiliary sources.

In Example 9, the subject matter of any one of Examples 1 to 8 can optionally further include that the sensor is configured as an irradiance sensor and the signal output the sensor is indicative of irradiance.

In Example 10, the subject matter of any one of Examples 1 to 9 can optionally further include that the source is configured to emit electromagnetic radiation in a non-visible wavelength range.

In Example 11, the subject matter of Example 10 can optionally further include that the non-visible wavelength range is included in the infrared wavelength range.

In Example 12, the subject matter of any one of Examples 1 to 11 can optionally further include that the source is configured to emit the electromagnetic radiation in a pulsed manner.

In Example 13, the subject matter of any one of Examples 1 to 12 can optionally further include that the source and the sensor are mounted in a fixed positional relationship relative to each other.

In Example 14, the subject matter of any one of Examples 1 to 13 can optionally further include a magnet assembly configured to generate a magnetic field in an emission region into which electromagnetic radiation is emitted by the source.

In Example 15, the subject matter of Example 14 can optionally further include that the magnet assembly comprises a plurality of magnets arranged such that a north pole of each magnet faces the emission region.

In Example 16, the subject matter of Example 15 can optionally further include that the magnets are disposed to surround the source.

What is claimed is:

1. A non-contact therapeutic irradiation device comprising:
   a light-emitting diode (LED) source configured to emit electromagnetic radiation in a predetermined spectral range;
   a sensor configured to detect electromagnetic radiation in the predetermined spectral range of the electromagnetic radiation emitted by the LED source and to output a signal indicative of a power of the detected radiation, wherein a predetermined magnitude range begins with a threshold value corresponding to a predetermined non-zero distance between the non-contact therapeutic irradiation device and a subject to be treated; and a controller configured to monitor a magnitude of the signal output by the sensor and to compare the magnitude of the signal with the predetermined magnitude range, wherein the magnitude of the signal lower than the predetermined magnitude range indicates the subject is too far away from the non-contact therapeutic irradiation device and is not receiving sufficient electromagnetic radiation in the predetermined spectral range, wherein the controller is configured to identify a time period during which the magnitude of the signal output by the sensor is included in the predetermined magnitude range, wherein the controller is configured to integrate the signal output by the sensor, if the magnitude of the signal is included in the predetermined magnitude range.

2. The non-contact therapeutic irradiation device of claim 1, further comprising at least one auxiliary LED source configured to emit an additional electromagnetic radiation in a wavelength range which is different from the wavelength range of the electromagnetic radiation emitted by the LED source.

3. The non-contact therapeutic irradiation device of claim 2, wherein the controller is configured to control the at least one auxiliary LED source on the basis of the signal output by the sensor.

4. The non-contact therapeutic irradiation device of claim 3, wherein the controller is configured to control the at least one auxiliary LED source such as to emit the additional electromagnetic radiation only if the magnitude of the signal output by the sensor is included in the predetermined magnitude range.

5. The non-contact therapeutic irradiation device of claim 4, wherein the predetermined spectral range is in an infrared range, wherein the additional electromagnetic radiation is in a visible range, and wherein the sensor includes a narrow optical bandpass filter matched to the predetermined spectral range.

6. The non-contact therapeutic irradiation device of claim 2, including a plurality of auxiliary LED sources.

7. The non-contact therapeutic irradiation device of claim 6, wherein at least two among the plurality of auxiliary LED sources are configured to emit electromagnetic radiation in mutually different wavelength ranges.

8. The non-contact therapeutic irradiation device of claim 6, wherein the controller is configured to individually control the auxiliary LED sources of the plurality of auxiliary LED sources.

9. The non-contact therapeutic irradiation device of claim 2, wherein the at least one auxiliary LED source comprises a plurality of groups of auxiliary LED sources, each group of auxiliary LED sources comprises a plurality of auxiliary LED sources, wherein each group is configured to emit electromagnetic radiation in a mutually different wavelength range, wherein each auxiliary LED source of a respective group is configured to emit electromagnetic radiation in an identical wavelength range.

10. The non-contact therapeutic irradiation device of claim 9, wherein the LED source, the sensor, and the plurality of groups of auxiliary LED sources are positioned relative to each other in a fixed rigid positional relationship, and wherein the LED source and the sensor are disposed centrally and the plurality of groups of auxiliary LED sources are disposed around the LED source and the sensor.

11. The non-contact therapeutic irradiation device of claim 9, wherein the sensor is configured to detect electromagnetic radiation in a wavelength range including the predetermined spectral range and each of the mutually different wavelength ranges.

12. The non-contact therapeutic irradiation device of claim 1, wherein the LED source is configured to emit the electromagnetic radiation in a non-visible wavelength range.

13. The non-contact therapeutic irradiation device of claim 12, wherein the non-visible wavelength range includes an infrared wavelength range.

14. The non-contact therapeutic irradiation device of claim 1, wherein the LED source is configured to emit the electromagnetic radiation in a pulsed manner.

15. The non-contact therapeutic irradiation device of claim 1, wherein the LED source and the sensor are mounted in a fixed positional relationship relative to each other.

16. The non-contact therapeutic irradiation device of claim 1, further comprising a magnet assembly configured to generate a magnetic field in an emission region into which the electromagnetic radiation is emitted by the LED source.

17. The non-contact therapeutic irradiation device of claim 16, wherein the magnet assembly comprises a plurality of magnets arranged such that a north pole of each magnet faces the emission region.

18. The non-contact therapeutic irradiation device of claim 17, wherein the magnets are disposed to surround the LED source in a ring pattern.

19. The non-contact therapeutic irradiation device of claim 1, wherein the LED source is permanently on during the operation of the non-contact therapeutic irradiation device to monitor the relative non-zero distance between the non-contact therapeutic irradiation device and the subject.

20. The non-contact therapeutic irradiation device of claim 1, wherein the predetermined spectral range is less than 10 nm wide and wherein the LED source is configured to emit the electromagnetic radiation having a power of one to three orders of magnitude higher than a power of an ambient radiation in the predetermined spectral range at room temperature.

* * * * *